US006851428B2

(12) United States Patent
Dennis

(10) Patent No.: US 6,851,428 B2
(45) Date of Patent: Feb. 8, 2005

(54) RESPIRATORY MASK

(75) Inventor: Carnell K. Dennis, 2402 Society Hill, Claymont, DE (US) 19703

(73) Assignee: Carnell K. Dennis, Wilmington, DE (US)

( * ) Notice: Subject to any disclaimer, the term of this patent is extended or adjusted under 35 U.S.C. 154(b) by 158 days.

(21) Appl. No.: 10/041,523

(22) Filed: Jan. 8, 2002

(65) Prior Publication Data

US 2003/0127101 A1 Jul. 10, 2003

(51) Int. Cl.$^7$ .............................................. A62B 18/02
(52) U.S. Cl. ........................... 128/205.25; 128/206.21; 128/206.28; 128/207.11
(58) Field of Search .......... 128/200.22, 201.12–201.17, 128/201.19, 201.22–202.11, 204.18, 205.25, 205.27–207.18, 200.24, 203.29

(56) References Cited

U.S. PATENT DOCUMENTS

| | | | |
|---|---|---|---|
| 3,977,432 A | | 8/1976 | Vidal |
| 4,657,010 A | | 4/1987 | Wright |
| 4,739,755 A | * | 4/1988 | White et al. ........... 128/206.12 |
| 4,793,342 A | * | 12/1988 | Haber et al. ........... 128/202.27 |
| 5,040,530 A | * | 8/1991 | Bauer et al. ........... 128/206.12 |
| 5,050,594 A | * | 9/1991 | Babb ..................... 128/206.24 |
| 5,353,789 A | * | 10/1994 | Schlobohm ............ 128/206.24 |
| 5,673,690 A | * | 10/1997 | Tayebi et al. .......... 128/206.24 |
| 5,921,239 A | * | 7/1999 | McCall et al. ......... 128/205.25 |
| 6,102,040 A | * | 8/2000 | Tayebi et al. .......... 128/206.24 |
| 6,474,336 B1 | * | 11/2002 | Wolfe .................... 128/206.21 |
| 2003/0062040 A1 | * | 4/2003 | Lurie et al. ............ 128/203.11 |

* cited by examiner

Primary Examiner—Glenn K. Dawson
(74) Attorney, Agent, or Firm—Connolly Bove Lodge & Hutz LLP

(57) ABSTRACT

A respiratory mask is reduced in size to better fit patients with smaller faces by either (a) folding one or more accordian folds formed in an upper portion of the mask, or (b) tearing away a part of the upper portion of the mask. The respiratory mask for adult patients can thus be adjusted to fit smaller adults and larger children. The respiratory mask for children can thus be adjusted to fit smaller children. A ball joint swivel connector is provided to connect the gas inlet of the masks to the hose connection for respiratory or nebulizer treating gases or aerosols.

35 Claims, 3 Drawing Sheets

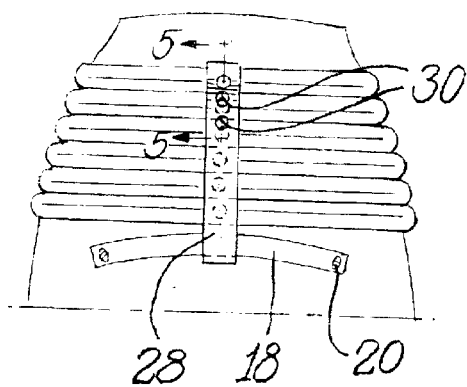
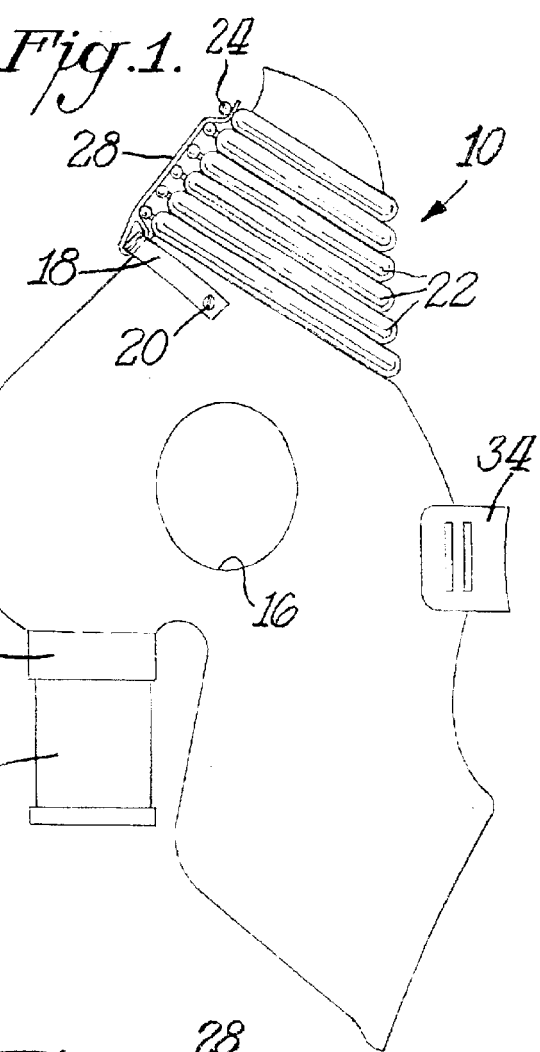
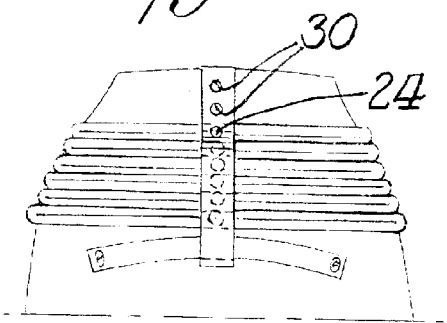
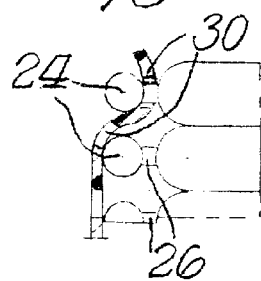
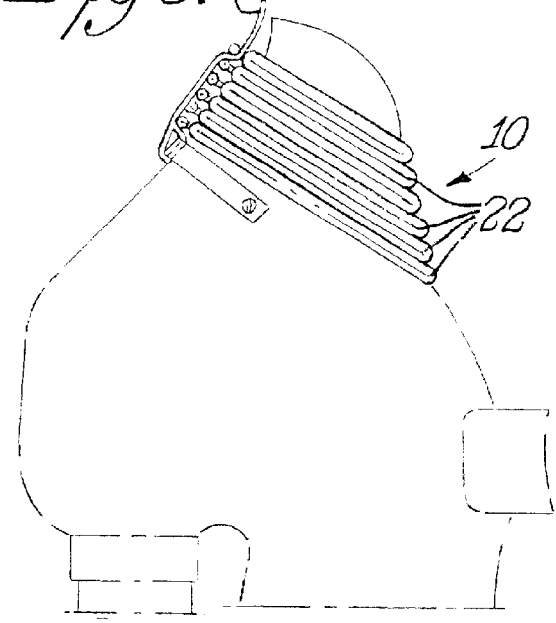

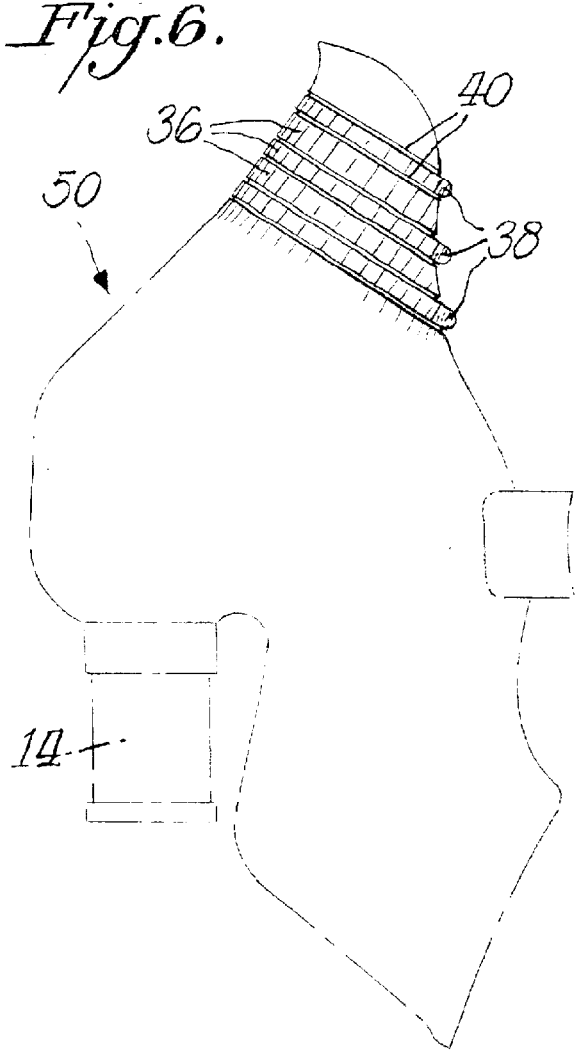
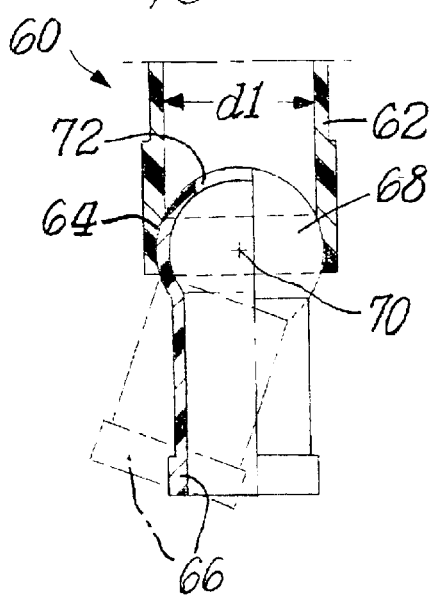
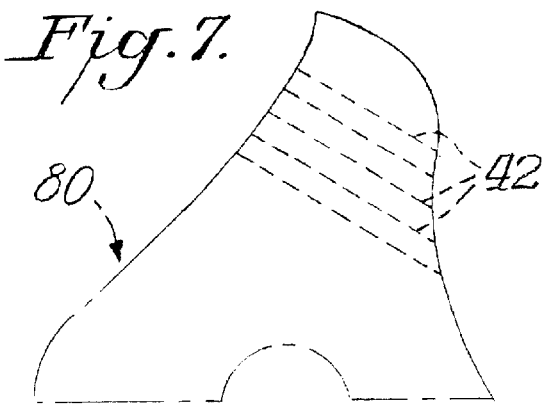
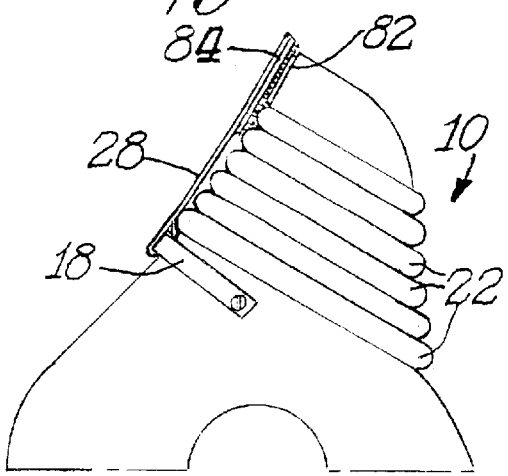

RESPIRATORY MASK

FIELD OF THE INVENTION

The present invention relates to respiratory masks used to administer treating gases or medications to patients. A representative treating gas is oxygen, and a representative medication is an aerosol for asthma treatment.

BACKGROUND OF THE INVENTION

Hospitals and respiratory therapists administer treating gases to individual patients by placing a respiratory mask over the patient's nose and mouth. The masks are supplied in standard sizes intended for adults and children. However, many adult patients have smaller facial dimensions such that the standard sizes do not fit properly, at best making the mask uncomfortable and at worst leading to ineffective administration of treating gases. In addition, many children have smaller facial dimensions such that the standard mask sizes provided for children do not fit them. Hence, an adjustable-size respiratory mask is needed to fit patients with smaller facial dimensions.

U.S. Pat. No. 4,657,010 discloses an adjustable face mask in which the bottom of the mask may be extended lengthwise by fastening a separate extension portion (lower portion 14) to the mask. The lower portion 14 is provided with snap closures 42 that mate with eyelet holes 40 in the upper portion of the mask. The separate extension portion is awkward, and size adjustments cannot effectively be made while the mask is in place over a patient's face. Most patient discomfort is caused when a too large size mask covers their eyes and/or forehead, making the bottom portion size adjustment in this prior patent less helpful when trying to solve the problems associated with over-sized respiratory masks. Moreover, the separate extension portion is more apt to be disconnected or lost before or during use.

Respiratory masks are provided with a generally rigid connector positioned proximate to the nose portion of the mask. A tube to introduce the treating gases is removably attached to the connector. A movable or swivelable connector would greatly ease or eliminate difficulties presently associated with connecting a tube or a nebulizer for treating gases to the respiratory mask. Such swivelable connector would be particularly advantageous for respiratory masks for nebulizer aerosol therapy used when treating smaller adults and children.

SUMMARY OF THE INVENTION

A size-adjustable respiratory mask has at least one accordian fold formed in an upper portion of the mask. The accordian fold has an open position, most suited when the mask is to be used for an average or larger size adult, and a folded position most suited when the mask is to be used for a smaller size adult. A button or snap is associated with the accordian fold. A band defining one or more openings is provided for receiving the button or snap associated with the accordian fold. The accordian fold is held in its folded position when the button or snap is received within one of the openings in the band. The length of the band and the position of the openings within the band determine the extent to which the accordian fold is held in its folded closed position or unfolded open position. If various openings are provided in the band, the accordian fold can be held in a folded position that is between the fully open and fully closed position.

Preferably, the accordian fold is formed by one or more ribs connected by a flexible material, or by one or more tubes connected by a flexible material. In the most preferred embodiment, the accordian fold is formed integrally in the upper portion of the mask. Most preferably, a plurality of accordian folds are provided.

The mask is constructed from one or more resilient plastic materials that are known as suitable for medical applications. Preferably, the mask material is latex free and free of other known allergens. Preferably, the mask is constructed from one or more of the following materials: thermoplastic resins, polyurethane resins, poly(vinyl chloride), polypropylene, polyethylene, polystyrene, SURLYN® from E. I. DuPont de Nemours & Company, Inc., or other plastics. A particularly preferred poly(vinyl chloride) is VM 1775 NT Clear 0001 from Maclin Company of City of Industry, Calif.

Presently, respiratory masks include a deformable strap bridging the upper portion of the mask. The deformable strap is formed of bendable metal and is bendable to conform to the contours of a patient's nose to hold the mask in place. In the preferred embodiment of the invention, the respiratory mask includes a deformable strap, and the proximal end of the band is anchored by the deformable strap. In this preferred embodiment, the distal end of the band defines the openings that mate with the snaps or buttons associated with the accordian fold or folds. The openings can be slits or eyelets or holes or reinforced grommets.

In an alternate embodiment, a size-adjustable respiratory mask has at least one strip formed in an upper portion of the mask, and the mask is made smaller to better conform to facial dimensions of a smaller patient by tearing the strip and separating the upper portion of the mask from a lower portion of the mask along a path defined by the strip. Preferably, more than one strip is formed in the upper portion of the mask, so that the size of the mask can be reduced to one of several different smaller sizes by choosing which strip to tear away. Most preferably, a series or a plurality of strips are aligned in parallel at the upper portion of the mask.

Each end of a strip may have a tear tab formed therein. The strip generally should be formed of a material that is more rigid than the material forming the mask so that when the strip is pulled, the upper portion of the mask will separate along the desired tear line or discontinuity defined by the strip. Most preferably, the mask material defines perforations adjacent to the strip.

Methods for adjusting the size of a respiratory mask to fit a patient with a smaller face are also claimed. In a first method, at least one accordian fold formed in an upper portion of the mask is folded from an open position to a closed position, and is then secured in its closed position by mating a button or snap associated with the accordian fold with an opening formed in a band. The proximal end of the band may be attached to an upper portion of the mask or to a deformable strap that is generally provided on respiratory masks to help secure the mask around the bridge of a patient's nose.

In a second method for adjusting the size of a respiratory mask, an upper portion of the mask is detached. Preferably, the upper portion is detached by pulling a tear strip associated with an upper portion of the mask. Perforations may be provided to facilitate separation of the upper portion of the mask from the lower portion of the mask. If perforations are provided, they generally should be adjacent to the tear strips. Alternatively, the tear strips may define a discontinuity in the material forming the mask such that a tear will progress along that discontinuity.

In yet another embodiment of the invention, a respiratory mask has a tubular inlet through which respiratory gas is introduced and a connector associated with such tubular inlet. The tubular inlet defines a distal end and a proximal end. The tubular inlet further defines a first inner diameter at its proximal end and has a concave annular groove at its distal end. The concave annular groove defines a second inner diameter that is greater than the first inner diameter of the tubular inlet.

The connector has a proximal end and a distal end and defines a gas inlet at its distal end and a gas outlet at its proximal end. The proximal end of the connector terminates into a ball swivel joint that is partially held within the concave annular groove in the tubular inlet. Preferably, the gas outlet is defined within the ball swivel joint. The ball swivel joint preferably has an outer diameter that is greater than the first inner diameter of the tubular inlet. The ball swivel joint defines a center of rotation and when the ball swivel joint is held within the concave annular groove in the tubular inlet, the center of rotation is positioned within the tubular inlet in a volume space therein defined by the annular groove. The connector is swivelable within the distal end of the tubular inlet to make it easier to adjust the position of the connector without removing the respiratory mask from the patient. The swivelable connection permits a technician to move the connector away from the patient's face when attaching a gas treatment tube or nebulizer to the connector.

DESCRIPTION OF THE FIGURES

FIG. 1 is a side elevational view of a respiratory mask according to a first embodiment of the invention as sized for an average adult patient;

FIG. 2 is a fragmental front elevational view of the respiratory mask of FIG. 1;

FIG. 3 is a side elevational view of a respiratory mask according to the invention as adjusted in size for a smaller adult patient;

FIG. 4 is a fragmental front elevational view of the respiratory mask of FIG. 3;

FIG. 5 is a cross-sectional view taken along line 5—5 of FIG. 2 showing size-adjusting means as a button held within an opening in a strap;

FIG. 6 is a side elevational view of a respiratory mask according to a second alternate embodiment of the invention as sized for an average adult patient;

FIG. 7 is a fragmental side elevational view of the respiratory mask of FIG. 6;

FIG. 8 is a fragmental partial cross-sectional view showing a ball swivel joint connector engaged within the tubular inlet of a respiratory mask;

FIG. 9 is a fragmental side elevational view of a respiratory mask according to a third alternate embodiment of the invention.

DESCRIPTION OF THE PREFERRED EMBODIMENTS

Figure 10:
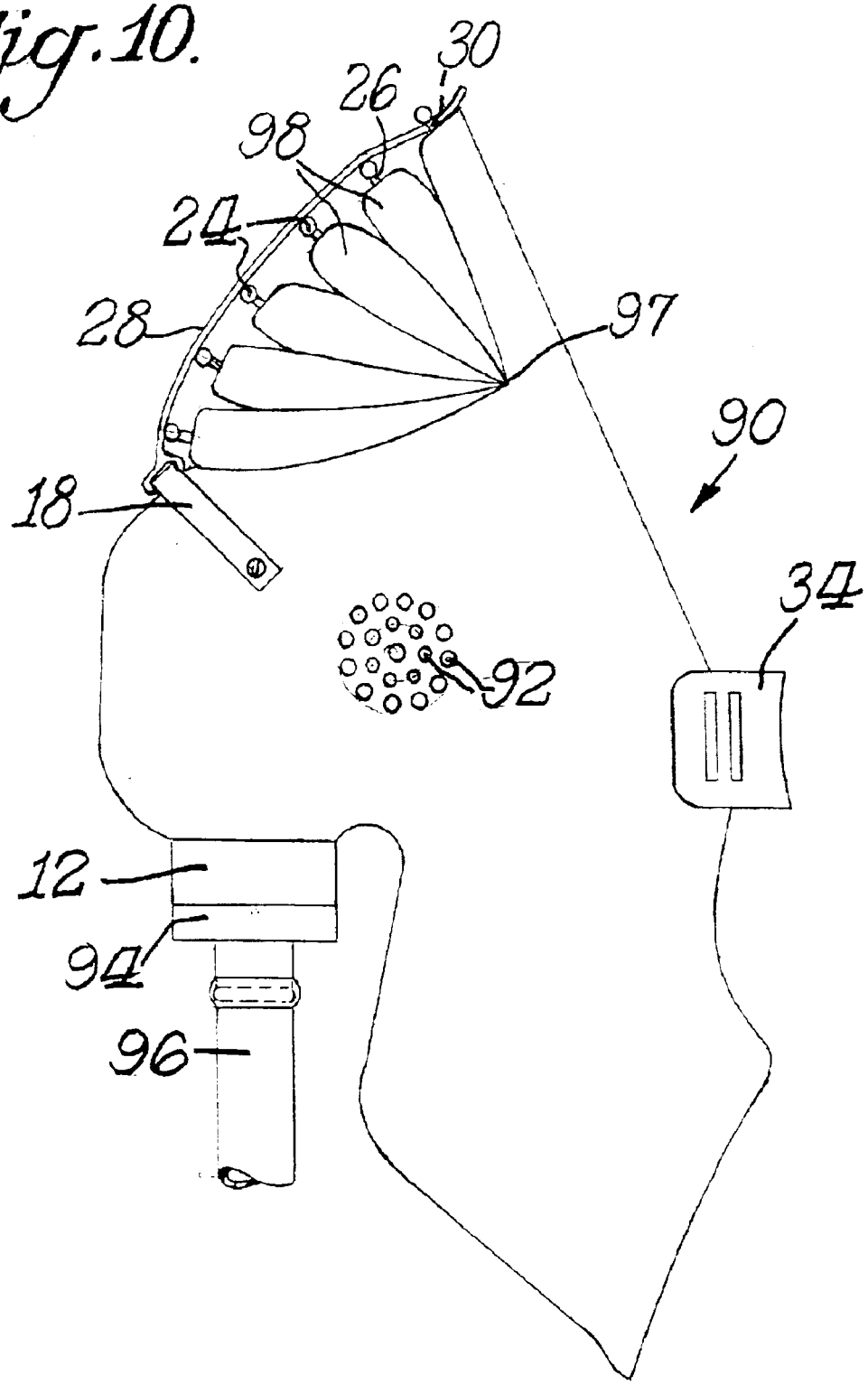
FIG. 10 is a side elevational view of a respiratory mask according to a fourth alternate embodiment of the invention as sized for an average adult patient.

Referring first to FIG. 1, a respiratory mask 10 includes a mask portion for covering the nose and mouth of a patient receiving a respiratory treatment, such as oxygen or a medicative aerosol or vapor. The mask 10 includes a tubular inlet 12 proximate the nose portion of the mask. A connector 14 is attached to the tubular inlet 12. A nebulizer (not shown) for delivering the respiratory treatment is in turn attached to the connector 14. The mask 10 further defines one or more exhaust ports 16, which are preferred when a mask is used for aerosol or vapor treatments. Head strap brackets 34 are attached to the lateral edges of the mask 10. One or more elastic head straps (not shown) are threaded through the brackets and wrap around the patient's head to hold the mask in place during treatment.

The mask 10 is provided with means for adjusting mask size. As shown in FIG. 1, the mask 10 is configured for a normal size adult male. The mask 10 is provided with a deformable metal strap 18 attached by snaps 20. The metal strap 18 can be bent over the bridge of the patient's nose to help hold the mask in place during treatment.

Accordian folds 22 are provided in a parallel array at the top of the nose portion of the mask 10. Each accordian fold comprises a rib or tube of stiffer material than the more resilient plastic material used to form the body of the mask. Each rib or tube is connected by lateral edge to an adjacent rib or tube. When expanded, as shown in FIG. 1, the mask 10 is of a size suitable for an adult male. Preferably, as shown in FIG. 1, the accordian folds 22 are integral with the material forming the top portion of the mask 10.

A snap or button 24 is associated with each accordian fold 22. The buttons 24 are mounted on pins 26 to separate slightly the buttons from the edges of the accordian folds 22. A band 28 is connected to the deformable metal strap 18 at its proximal end and defines one or more openings 30 at its distal end. The band 28 is formed from poly(vinyl chloride) resin or plastic material. Preferably, the band 28 has a thickness comparable to the distance of separation between the buttons 24 and the accordian folds 22. As shown in FIGS. 1, 2 and 5, the uppermost button is held within the most distant hole in the band 28. It would also be possible to leave the distal portion of the band 28 unattached to any button 24 associated with the accordian folds. In the preferred embodiment, the accordian folds 22 can be expanded to a fully open position such that the mask is suitable for use by a larger adult.

The means for attaching the band 28 to a button 24 associated with an accordian fold 22 is shown in FIG. 5. The openings 30, such as eyelet holes, have an inner diameter slightly smaller than the outer diameter of the buttons 24. Each opening or hole 30 in the band 28 can be snap fit over a button 24. The snap connection is not permanent, and an adjustment can be made readily by disconnecting the band from a particular button and reattaching to another button.

Various size adjustments are possible. Referring next to FIGS. 3 and 4, the mask 10 is shown with the accordian folds 22 folded to a closed position to reduce the mask size. In this embodiment, the third opening or hole in the band 28 engages the uppermost button, thus pulling the button and the associated accordian fold 22 tighter toward the deformable strap 18 bridging the nose portion of the mask 10. With the accordian folds 22 compressed and folded to a closed position, the mask 10 is better suited for use by a smaller adult, such as a woman weighing under 100 pounds, or by a teenager or child. Folding the accordian folds may result in substantially linear contraction of the upper portion of the mask.

Preferably, the mask 10 is fabricated from nonallergenic materials known to be suitable for contacting a patient's skin. Such materials include: thermoplastic resins, polyurethane resins, poly(vinyl chloride), polypropylene, polyethylene, polystyrene, SURLYN® from E. I. DuPont de Nemours & Company, Inc., or other plastics. The preferred mask 10 is formed from a clear poly(vinyl chloride) resin or plastic (with a thickness of about 0.020 inch) so that a respiratory technician or health care worker can observe the patient's face while treatments are administered. A particularly preferred poly(vinyl chloride) is VM 1775 NT Clear 0001 from Maclin Company of City of Industry, Calif.

A second preferred embodiment of the respiratory mask 10 is shown in FIG. 9, wherein the band 28 is provided with a hook strip 84 of a hook and loop fastener (such as a VELCRO® fastener) and the upper surface of the mask is provided with a loop strip 82. The size of the mask 10 is then adjusted by compressing or folding the accordian folds 22 and causing the hook strip 84 to contact the loop strip 82 to fasten the band 28 to the upper surface of the mask 10 to maintain the accordian folds in a folded position.

A third preferred embodiment of the respiratory mask 50 is shown in FIGS. 6 and 7. Like parts are numbered with the same reference numerals used in FIGS. 1–5. Rather than using accordian folds 22 (e.g., FIG. 1), the mask 50 incorporates a series of tear strips 36 that have tear tabs 38 at one or both ends. Preferably, the tear strips 36 are integral with the material forming the mask 50 and are separated by grooves 40 or other discontinuities in the thickness of the material. To reduce the size of the mask 50, one of the tear strips 36 is pulled away from the mask to separate the tear strip 36 and the upper portion of the mask 50 above the strip from the remaining lower portion of the mask.

As an alternative to the grooves 40, perforations 42 (FIG. 7) may be provided in the mask material to guide the tearing away of material to reduce the size of the mask 80. The strips may be formed of a material that is more rigid than adjacent material forming the mask.

The embodiment of the invention shown in FIGS. 1–5 permits variable adjustment of the mask size from larger to smaller. Moreover, once the mask is adjusted to a smaller size, it may still be enlarged to the original adult size or any size therebetween. The embodiments of the invention shown in FIGS. 6 and 7, however, do not provide a means for returning the mask to its original adult size following the size adjustment made by removing material from the top portion of the mask. Nevertheless, the embodiments of FIGS. 6 and 7 may have fabrication or cost advantages making them suitable for many applications.

Referring next to FIG. 10, an oxygen mask 90 has small respiration exhaust holes 92 formed in a pattern of concentric rings in each side mask surface. Rather than a connector as shown in earlier mask embodiments, the oxygen mask 90 has a plug 94 attached to the tubular inlet 12. The plug 94 has a nipple to which is attached a separate tube 96 for introducing oxygen to the patient. A series of angular tapered accordian folds 98 are formed in the mask material above the nose portion, with each fold terminating at pivot point 97. When the folds 98 are expanded, as shown in FIG. 10, the mask 90 is of a size suitable for an adult male. Preferably, as shown in FIG. 10, the accordian folds 98 are integral with the material forming the top portion of the mask 90.

A snap or button 24 is associated with each accordian fold 98. The buttons 24 are mounted on pins 26 to separate slightly the buttons from the edges of the accordian folds 98. A band 28 is connected to the deformable metal strap 18 at its proximal end and defines one or more openings 30 at its distal end. The band 28 is formed from poly(vinyl chloride) resin or plastic material. Preferably, the band 28 has a thickness comparable to the distance of separation between the buttons 24 and the accordian folds 22. As shown in FIG. 10, the uppermost button is held within the most distant hole in the band 28. It would also be possible to leave the distal portion of the band 28 unattached to any button 24 associated with the accordian folds. In the preferred embodiment, the accordian folds 22 can be expanded to a fully open position such that the mask is suitable for use by a larger adult.

The size of the mask 90 is reduced to better fit the face of a smaller adult or a teenager or child by creasing or folding the mask material along the accordian folds 98. The folds are held in such creased or folded position by inserting one or more of the buttons 24 into holes or openings 30 in the band 28. Because the folds 98 have a tapered shape that terminates at point 97, they can be folded to reduce the mask size yet still permit the contours of the outer edges of the mask to better conform to the patient's face.

Each of the masks 10, 50, 80 and 90 may be modified also by incorporating a swivel joint connection as shown in FIG. 8. The inlet tube 62 has an inner diameter d1 at its proximal end and an annular groove 64 formed in its distal end. The inlet tube 62 usually is integral with the respiratory mask, and generally depends from a central portion of the mask that is proximate to a patient's nose when the mask is placed on a patient for respiratory treatment.

A connector 66 is snap fit into the inlet tube 62 during manufacture. The connector 66 has a tubular distal end and a ball joint 68 formed at its proximal end. The ball joint 68 defines an opening 72 such that the connector communicates with the inlet tube to permit gases or treating fluids to flow therethrough. The ball joint 68 is held within the annular groove 64 of the inlet tube 62. The ball joint 68 defines a center point 70 about which the ball joint may swivel. The center point 70 is positioned within the volume defined by the inlet tube between the uppermost edge of the annular groove and the lowermost edge of the annular groove. With this placement, the connector 66 swivels with respect to the inlet tube 62 so that the distal end of the connector can be moved away from a patient's face when a source tube for a gas treatment or a nebulizer is being connected. In addition, the swivel connection permits the patient to adjust the angle of the source tube for increased comfort.

While specific embodiments of the invention have been described and illustrated, such embodiments should be considered illustrative of the invention only and not as limiting the invention as construed in accordance with the accompanying claims.

I claim:

1. A size-adjustable respiratory mask, comprising:

a plurality of accordian folds formed in an upper portion of the mask;

a button or snap associated with the accordian folds; and a band defining one or more openings for receiving the button or snap and extending generally along a length of the mask, wherein said accordian folds have an open position and a folded position and are held in their folded positions when the button or snap is received within one of the openings in the band, wherein the accordian folds allow shortening of a length of the mask, wherein the mask can be made smaller to better conform to the facial dimensions of a patient by folding the accordian folds into folded positions that cause the mask to have a smaller length than when the accordian folds are in their open positions, and wherein folding the accordian folds results in substantially linear contraction of the upper portion of the mask.

2. The mask of claim 1, wherein the accordian folds are formed by one or more ribs connected by a flexible material.

3. The mask of claim 1, wherein the accordian folds are formed integrally in the upper portion of the mask.

4. The mask of claim 1, wherein the mask is formed from a resilient plastic material selected from the group consisting of: thermoplastic resins, polyurethane resins, poly(vinyl chloride), polypropylene, polystyrene and polyethylene.

5. The mask of claim 1, wherein the mask once made smaller by folding the accordian folds can be made larger by expanding the accordion folds to their open positions.

6. The mask of claim 1, wherein the length of the mask extends along a vertical extent of the mask.

7. A size-adjustable respiratory mask, comprising:
at least one accordian fold formed in an upper portion of the mask;
a button or snap associated with the accordian fold; and
a band defining one or more openings for receiving the button or snap and extending generally along a length of the mask,
wherein said accordian fold has an open position and a folded position and is held in its folded position when the button or snap is received within one of the openings in the band,
wherein the accordian fold is formed by one or more tubes connected by a flexible material,
wherein the mask can be made smaller to better conform to the facial dimensions of a patient by folding the accordian folds into folded positions that cause the mask to have a smaller length than when the accordian folds are in their open positions, and wherein
folding the accordian folds results in substantially linear contraction of the upper portion of the mask.

8. A size-adjustable respiratory mask, comprising:
at least one accordian fold formed in an upper portion of the mask;
a button or snap associated with the accordian fold; and
a band defining one or more openings for receiving the button or snap and extending generally along a length of the mask,
wherein said accordian fold has an open position and a folded position and is held in its folded position when the button or snap is received within one of the openings in the band,
and wherein the accordion fold tapers to a pivot point,
wherein the mask can be made smaller to better conform to the facial dimensions of a patient by folding the accordian folds into folded positions that cause the mask to have a smaller length than when the accordian folds are in their open positions, and wherein
folding the accordion folds results in substantially linear contraction of the upper portion of the mask.

9. A size-adjustable respiratory mask, comprising:
at least one accordian fold formed in an upper portion of the mask;
a button or snap associated with the accordian fold;
a band defining one or more openings for receiving the button or snap and extending generally along a length of the mask; and
a deformable strap bridging the upper portion of the mask,
wherein said accordian fold has an open position and a folded position and is held in its folded position when the button or snap in received within one of the openings in the band,
wherein the mask can be made smaller to better conform to the facial dimensions of a patient by folding the accordian folds into folded positions that cause the mask to have a smaller length than when the accordian folds are in their open positions, and wherein
folding the accordian folds results in substantially linear contraction of the upper portion of the mask.

10. The mask of claim 9, wherein the deformable strap is formed of bendable metal and is bendable to conform to the contours of a patient's nose to hold the mask in place.

11. The mask of claim 9, wherein the band has a proximal end and a distal end, and the proximal end is attached to the deformable strap.

12. The mask of claim 11, wherein the distal end of the band defines the openings.

13. The mask of claim 12, wherein the openings are eyelets.

14. A size-adjustable respiratory mask, comprising:
at least one strip formed in an upper portion of the mask; wherein said mask can be made smaller to better conform to facial dimensions of a patient by tearing the strip and separating the upper portion of the mask from a lower portion of the mask along a path defined by the strip,
and wherein the strip has a proximal end and a distal end and a tear tab is formed at the proximal end.

15. The mask of claim 14, wherein a second tear tab is formed at the distal end.

16. A size-adjustable respiratory mask, comprising:
at least one strip formed in an upper portion of the mask; wherein said mask can be made smaller to better conform to facial dimensions of a patient by tearing the strip and separating the upper portion of the mask from a lower portion of the mask along a path defined by the strip,
and wherein the strip is formed of a material that is more rigid than adjacent material forming the mask.

17. A size-adjustable respiratory mask, comprising:
at least one strip formed in an upper portion of the mask; wherein said mask can be made smaller to better conform to facial dimensions of a patient by tearing the strip and separating the upper portion of the mask from a lower portion of the mask along a path defined by the strip,
and wherein the mask defines perforations adjacent to the strip such that the strip is rippable away from the remainder of the mask along the perforations.

18. The mask of claim 17, further comprising a plurality of strips formed in the upper portion of the mask.

19. The mask of claim 18, wherein the plurality of strips are aligned in parallel.

20. The mask of claim 17, wherein the perforations form a discontinuity along which the upper portion of the mask may be separated from a lower portion of the mask.

21. A method of adjusting a respiratory mask to fit a patient with a smaller face, comprising:
folding at least one accordian fold formed in an upper portion of the mask from an open position to a closed position; and
securing the accordian fold in its closed position by mating a button or snap associated with the accordian fold with an opening formed in a band,
wherein the band has a proximal end and a distal end and the opening in the band is formed in its distal end, and wherein a deformable strap is attached to the mask and the proximal end of the band is attached to the strap.

22. The method of claim 21, wherein the proximal end is attached to an upper portion of the mask.

23. A method of adjusting a respiratory mask to fit a patient with a smaller face, comprising:
   detaching an upper portion of the mask,
   wherein the upper portion is detached by pulling a tear strip associated with an upper portion of the mask.

24. A method of adjusting a respiratory mask to fit a patient with a smaller face, comprising:
   detaching an upper portion of the mask,
   wherein the upper portion is detached by separating the upper portion from a lower portion of the mask along perforations provided in the mask between the upper and lower portions of the mask.

25. A size-adjustable respiratory mask, comprising:
   at least one accordian fold formed in an upper portion of the mask;
   a first fastening member attached to a surface of the mask; and
   a band extending generally along a length of the mask and having a second fastening member attached thereto, said second fastening member engageable with said first fastening member,
   wherein said accordian fold has an open position and a folded position and is held in its folded position when the first fastening member engages the second fastening member,
   wherein the accordian fold is formed by one or more tubes connected by a flexible material,
   wherein the mask can be made smaller to better conform to the facial dimensions of a patient by folding the accordian fold into a folded position that causes the mask to have a smaller length than when the accordian fold is in its open position, and wherein
   folding the accordian fold results in substantially linear contraction of the upper portion of the mask.

26. The mask of claim 25, wherein the accordian fold is formed integrally in the upper portion of the mask.

27. The mask of claim 25, wherein the mask is formed from a resilient plastic material selected from the group consisting of: thermoplastic resins, polyurethane resins, poly (vinyl chloride), polypropylene, polystyrene and polyethylene.

28. The mask of claim 25, further comprising:
   a deformable strap bridging the upper portion of the mask.

29. The mask of claim 28, wherein the deformable strap is formed of bendable metal and is bendable to conform to the contours of a patient's nose to hold the mask in place.

30. The mask of claim 28, wherein the band has a proximal end and a distal end, and the proximal end is attached to the deformable strap.

31. The mask of claim 30, wherein the second fastening member is attached to the distal end of the band.

32. The mask of claim 25, wherein the first fastening member is a loop strip and the second fastening member is a hook strip.

33. The mask of claim 25, wherein the first fastening member is a hook strip and the second fastening member is a loop strip.

34. The mask of claim 25, wherein the mask once made smaller by folding the accordian fold can be made larger by expanding the fold to its open position.

35. A size-adjustable respiratory mask, comprising;
   a plurality of accordian folds formed in an upper portion of the mask;
   a first fastening member attached to a surface of the mask; and
   a band extending generally along a length of the mask and having a second fastening member attached thereto, said second fastening member engageable with said first fastening member,
   wherein the accordian folds have an open position and a folded position and is held in its folded position when the first fastening member engages the second fastening member,
   wherein the accordian folds are formed by a plurality of ribs connected by a flexible material,
   wherein the mask can be made smaller to better conform to the facial dimensions of a patient by folding the accordian folds into folded positions that cause the mask to have a smaller length than when the accordian folds are in their open positions, and wherein
   folding the accordian folds results in substantially linear contraction of the upper portion of the mask.

* * * * *